(12) United States Patent
Novatzky et al.

(10) Patent No.: US 9,152,759 B2
(45) Date of Patent: Oct. 6, 2015

(54) KEY IMAGE NOTE MATCHING BY IMAGE HANGING PROTOCOLS

(75) Inventors: Benjamin D. Novatzky, Oak Park, IL (US); Himanshu Jay Mehta, Chicago, IL (US)

(73) Assignee: General Electric Company, Schenectady, NY (US)

( * ) Notice: Subject to any disclaimer, the term of this patent is extended or adjusted under 35 U.S.C. 154(b) by 2222 days.

(21) Appl. No.: 11/496,197

(22) Filed: Jul. 31, 2006

(65) Prior Publication Data

US 2008/0025585 A1   Jan. 31, 2008

(51) Int. Cl.
*G06F 17/00* (2006.01)
*G06F 19/00* (2011.01)
*G06T 7/00* (2006.01)
*G06F 17/24* (2006.01)

(52) U.S. Cl.
CPC ............ *G06F 19/321* (2013.01); *G06F 17/241* (2013.01); *G06F 19/3418* (2013.01); *G06T 7/0012* (2013.01)

(58) Field of Classification Search
CPC . G06F 19/321; G06F 19/3418; G06F 17/241; G06T 7/0012
See application file for complete search history.

(56) References Cited

U.S. PATENT DOCUMENTS

| 6,795,094 B1* | 9/2004 | Watanabe et al. ............. 715/762 |
| 7,010,751 B2* | 3/2006 | Shneiderman ................ 715/232 |
| 7,216,295 B2* | 5/2007 | Wu et al. ........................ 715/203 |
| 2006/0238546 A1* | 10/2006 | Handley et al. ............... 345/619 |

OTHER PUBLICATIONS

Diakopoulos et al.,"Mediating photo collage authoring," in Proc. UIST '05, © Oct. 23-27, 2005, ACM, pp. 183-186.*
Web site information: www.ihe.net/Technical_Framework/upload/ihe_tf rev.6.0ft_vol1_2005-05-20.pdf, Integrating the Healthcare Enterprise, IHE Technical Framework, vol. 1, Integration Profiles, Revision 6.0—Final Text, May 20, 2005.

* cited by examiner

*Primary Examiner* — Cesar Paula
*Assistant Examiner* — James H Blackwell
(74) *Attorney, Agent, or Firm* — Hanley, Flight and Zimmerman, LLC

(57) ABSTRACT

Certain embodiments of the present invention provide an image display method including selecting an image hanging protocol and displaying an image set based at least in part on the image hanging protocol. The image hanging protocol includes a rule set for displaying the image set based at least in part on a key image note. Certain embodiments of the present invention provide an image display system including a display device adapted to display an image set based at least in part on an image hanging protocol. The image hanging protocol includes a rule set for displaying the image set based at least in part on a key image note. Certain embodiments of the present invention provide an image hanging protocol including a rule set for displaying the image set based at least in part on a key image note.

23 Claims, 6 Drawing Sheets

KEY IMAGE NOTE MATCHING BY IMAGE HANGING PROTOCOLS

BACKGROUND OF THE INVENTION

The present invention generally relates to an improvement in the selection and presentation of medical imaging studies. More specifically, the present invention relates to key image note matching by image hanging protocols.

Picture archiving and communication systems ("PACS") connect to medical diagnostic imaging devices and employ an acquisition gateway (between the acquisition device and the PACS), storage and archiving units, display workstations, databases, and sophisticated data processors. These components are integrated together by a communication network and data management system. A PACS has, in general, the overall goals of streamlining health-care operations, facilitating distributed remote examination and diagnosis, and improving patient care.

A typical application of a PACS system is to provide one or more medical images for examination by a medical professional. For example, a PACS system can provide a series of x-ray images to a display workstation where the images are displayed for a radiologist to perform a diagnostic examination. Based on the presentation of these images, the radiologist can provide a diagnosis. For example, the radiologist can diagnose a tumor or lesion in x-ray images of a patient's lungs.

A series or sequence of a plurality of medical images is an imaging study. In general, an imaging study that is the most recent imaging study of a patient or is the imaging study currently being examined by a radiologist will be referred to as a current imaging study.

In order to properly diagnose a current imaging study, a radiologist must examine one or more previously acquired images of the same patient and compare these images to images of a current study. An imaging study that includes two or more previously acquired images is a historical imaging study. Furthermore, a historical imaging study whose images are relevant for comparing with the images of a current imaging study is a comparison imaging study. For example, images that are associated with or display the same anatomy are relevant for comparison purposes.

The images of an imaging study are displayed in a particular spatial layout and/or temporal sequence. In other words, the images may be displayed in certain positions on a display device relative to each other (a spatial layout, for example). The images may also be displayed in a certain ordered sequence by displaying image A first, followed by image B, followed by image C, and so on (a temporal sequence, for example). The spatial and/or temporal presentation of images is directed by a set of display rules. A display rule may include a set of instructions stored on a computer-readable media that direct the presentation of images on a display workstation. A set of display rules is known as an image hanging protocol. In general, an image hanging protocol is a series of display rules that dictate the spatial and/or temporal layout and presentation of a plurality of images.

Image hanging protocols are used in current PACS systems to present images of a diagnostic study for display. Image hanging protocols allow a user to specify studies for population into image layouts or regions, as well as the appearance of the layouts or regions. Furthermore, the user may specify which image hanging protocols are used to display which studies. The idea is to automate the presentation of images in the way most desired by the user.

Integrating the Healthcare Enterprise ("IHE") introduced the concept of a Key Image Note ("KIN"). A KIN is a note that marks one or more images in a study as significant, and specifies why the images are significant. More particularly, the KIN specifies image significance through KIN Title/Subtitles, which are defined by the DICOM standard. For example, to mark images to be shown to patient, one could create a KIN whose Title is "For Patient" and which references those images. As another example, to mark images as having quality artifact issues, one could create a KIN with a Title of "Quality Issue", a Subtitle of "Image artifact(s)", and which references those images.

A KIN may include a title, and optionally, a subtitle, a creation date, a creation time, a creator, and/or a creator type. Some users may be interested in some KIN categories more so that other KIN categories. For example, a surgeon may be interested in "For Surgery" KIN images. As another example, an instructor at a teaching institution may be interested in "For Teaching" and "For Research" KIN images. As another example, a primary care physician may be interested in "For Referring Provider" and "Best In Set" KIN images.

Furthermore, the KIN Titles/Subtitles are fully extensible by DICOM. Therefore, a user could create custom KIN categories or types, and utilize the custom KIN category or type to zero in on images of a specific interest. For example, a user may be interested in KIN images created by a radiologist or KIN images created by a technologist. As another example, a user may be interested in the most recent KIN images.

Current PACS systems implement image hanging protocols and KINs. However, finding and displaying relevant key images (e.g., KIN images) upon displaying the images of a study is a manual process and requires a user to perform several steps. For example, a user first selects a default image hanging protocol. The default image hanging protocol loads all images in a study. Next, the user selects a KIN. The selected KIN images are then loaded into an image layout. These steps are cumbersome, time-consuming, and inefficient for the user, especially in studies involving high volumes of images and KINs.

Thus, there is a need for an efficient way for a user to view images of interest upon the display of a study. This is especially true for environments where time is critical. For example, physicians in the Emergency Room or surgeons in the Operating Room need to be able to view "For Physician" and "For Surgery" KIN images as efficiently as possible. Even for a radiologist or other user, elimination of time lost due to extra steps in a workflow can greatly contribute to the efficiency and the quality of healthcare.

BRIEF SUMMARY OF THE INVENTION

Certain embodiments of the present invention provide a method for image display. The method includes selecting an image hanging protocol and displaying an image set based at least in part on the image hanging protocol. The image hanging protocol includes a rule set for displaying the image set based at least in part on a key image note.

Certain embodiments of the present invention provide a system for image display. The system includes a display device adapted to display an image set based at least in part on an image hanging protocol. The image hanging protocol includes a rule set for displaying the image set based at least in part on a key image note.

Certain embodiments of the present invention provide a computer-readable storage medium. The computer-readable storage medium includes a set of instructions for execution on a computer. The set of instructions includes a image display routine configured to display an image set based at least in part on an image hanging protocol. The image hanging protocol includes a rule set for displaying the image set based at least in part on a key image note.

Certain embodiments of the present invention provide an image hanging protocol. The image hanging protocol includes a rule set for displaying the image set based at least in part on a key image note.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Figure 1:
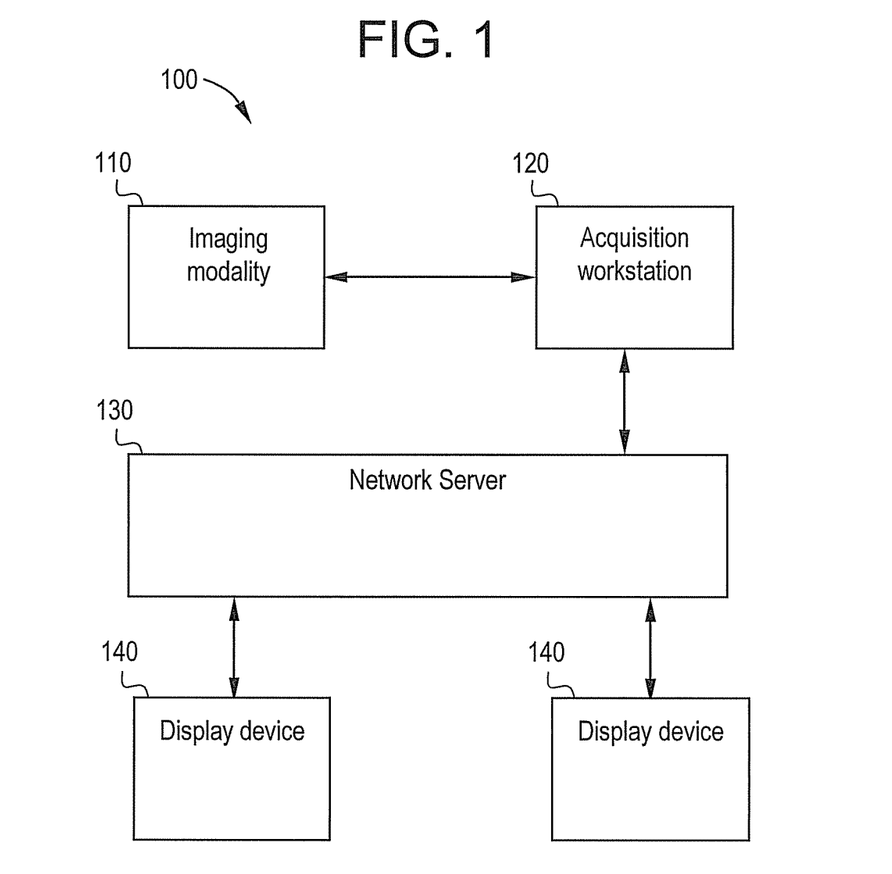
FIG. 1 illustrates an exemplary PACS system according to an embodiment of the present invention.

FIG. 1 illustrates an exemplary PACS system 100 according to an embodiment of the present invention. PACS system 100 includes an imaging modality 110, an acquisition workstation 120, a network server 130, and two display devices 140. While system 100 is illustrated in FIG. 1 as including a single imaging modality 110, a single acquisition workstation 120, a single network server 130, and two display devices 140, system 100 can include any number of imaging modalities 110, acquisition workstations 120, network servers 130, and/or display devices 140. In other words, no embodiment of the present invention is in any way limited to the illustration of system 100 as illustrated in FIG. 1.

Imaging modality 110 is capable of communicating with acquisition workstation 120. Acquisition workstation 120 is capable of communicating with imaging modality 110 and server 130. Server 130 is capable of communicating with acquisition workstation 120 and display devices 140. Display devices 140 are capable of communicating with server 130. In another embodiment of the present invention, display devices 140 may also communicate directly with acquisition workstation 120.

In operation, imaging modality 110 obtains one or more images of a patient anatomy. Imaging modality 110 can include any device capable of capturing an image of a patient anatomy, such as a medical diagnostic imaging device. For example, imaging modality 110 can include am x-ray imager, ultrasound scanner, magnetic resonance imager, computed radiography/tomography imager, nuclear imager, or the like. Image data representative of the image(s) is communicated between imaging modality 110 and acquisition workstation 120. The image data can be communicated electronically over a wired or wireless connection, for example.

Acquisition workstation 120 may apply one or more preprocessing functions to the image data. The preprocessing functions may be employed to prepare the image(s) for viewing on one or more display devices 140 and/or to prepare the image(s) for storage at one or more of display devices 140 and server 130. For example, acquisition workstation 120 may convert raw image data into a DICOM standard format or attach a DICOM header. In another example, a preprocessing function may include contrast or frequency preprocessing of an image.

Acquisition workstation 120 may attach or associate image data attributes with the image(s). An image data attribute can include any electronically communicable data representative of information relevant to the image(s), patient, patient anatomy, and/or medical or imaging procedure, for example. Exemplary image data attributes include data representative of an imaging procedure, one or more DICOM tag(s) and/or one or more patient anatomies or mapped anatomies.

An image data attribute representative of an imaging procedure can include data representative of the procedures used to obtain the image(s) (to which the image data attribute is attached or associated). An imaging procedure can include a sequence of imaging steps used to obtain one or more images. For example, an imaging procedure can include the insertion of a contrast agent in a patient and then taking one or more images of the patient anatomy that includes the contrast agent. In another example, an imaging procedure may include the acquisition of one or more images without using any sort of contrast agent.

An imaging procedure may include the taking of one or more images of a certain patient anatomy. For example, an imaging procedure may identify which patient anatomy (such as a patient's head, neck or chest) is featured or shown in one or more images, for example.

An imaging procedure may also include the particular imaging modality used to obtain one or more images and/or particular type or class of imaging modality used to obtain one or more images. A particular imaging modality may be a certain or particular imaging modality device of a plurality of imaging modality devices. In another example, a particular type or class of imaging modality may be a C-arm x-ray imaging device, magnetic resonance ("MR") imaging device, etc.

An imaging procedure may also include a representation of a user that employed an imaging modality to obtain the image(s). For example, an imaging procedure may include a representation of an identity of a radiologist who used an MR imaging device to obtain the image(s).

An image data attribute may include data representative of one or more DICOM tags. A DICOM tag may be attached to or associated with image data by imaging modality 110 and/or acquisition workstation 120. A DICOM tag may include any data specified by the DICOM Standard or any custom data allowed for by the DICOM Standard. For example, a DICOM tag may include image display data (e.g., (7FE0, 0010) Pixel Data), image data characteristics (e.g., (0028, 0002) Samples Per Pixel, (0028,0004) Photometric Interpretation), image capture characteristics (e.g., (0018,1050) Spatial Resolution, (0018,5101) View Position), anatomy data (e.g., (0018,0015) Body Part Examined), imaging device data (e.g., (0008,0060) Modality, (0008,1090) Manufacturer's Model Name), study-specific data (e.g., (0008,0020) Study Date, (0008,0030) Study Time), patient-specific data (e.g., (0010,0010) Patient's Name, (0010,0030) Patient's Birth Date), or any other data allowed for by the DICOM Standard.

An image data attribute may include data representative of a patient anatomy. Such data may include one or more mapped body parts. A mapped body part is any body part or anatomy featured in the image(s). An image data attribute that includes a mapped body part may be input by a user of system 100. For example, a radiologist may list or statically map the body part(s) or anatomy(ies) to be examined in an imaging procedure and/or featured in one or more images. Such a list may be attached to or associated with the image(s) as an image data attribute.

The image data (and associated image data attribute(s)) may then be communicated between acquisition workstation 120 and server 130. The image data may be communicated electronically over a wired or wireless connection.

In another embodiment of the present invention, as described above, image data (and associated image data attribute(s)) may be directly communicated between acquisition workstation 120 and one or more display devices 140. The image data and image data attribute(s) may be communicated over a wired or wireless connection.

Server 130 can include any computer-readable storage and retrieval device that is accessible over an intranet or over the Internet. Server 130 can include a computer-readable storage medium suitable for storing the image data for later retrieval and viewing at a display device 140. Server 130 can also include a computer-readable storage medium suitable for storing one or more image hanging protocols and/or key image notes (KINs), as described in more detail below.

Images (and associated image data attributes) and/or one or more image hanging protocols and/or KINs may be communicated between server 130 and one or more display devices 140. The image data and associated image data attribute(s) and/or comparison rules may be communicated over a wired or wireless connection or transferred on a physical media, such as magnetic tape.

One or more display devices 140 are capable of communication with or configured to communicate with server 130. A display device 140 can include any device capable of displaying an imaging study. An imaging study is a group of one or more images. An imaging study may be used in a PACS system to make a diagnosis based on one or more images. For example, as described above, a radiologist using system 100 may employ a display device 140 to analyze a series of images of a patient's lungs. The radiologist may use the images to determine whether the patient's lungs include a tumor.

As described above, display devices 140 can include any device capable of presenting an imaging study. For example, one exemplary display device 140 includes a display workstation in a PACS system. A display workstation 140 can include a general purpose processing circuit, a network server 130 interface, a software memory, an input device (such as a keyboard, mouse, stylus, microphone, etc.) and an output device (such as an image display monitor or computer monitor), for example. The network server 130 interface may be implemented as a network card connecting to a TCP/IP based network, but may also be implemented as a parallel port, USB, or FireWire interface, for example. While one exemplary display device 140 is described, this example should not be construed as limiting the present invention to just one display device 140. As described above, a display device 140 includes any device capable of presenting or displaying an imaging study to a user. Therefore, a display device 140 may also be embodied in a wireless display device, for example.

As described above, display devices 140 may retrieve or receive image data (for example, an imaging study) from server 130 for display to one or more users. For example, a display device 140 may retrieve or receive an imaging study that includes a computed radiography ("CR") image of a patient's chest. A radiologist may then examine the image as displayed on a display device for any objects of interest such as, tumors, lesions, etc.

Display devices 140 may also be capable of retrieving/receiving or configured to retrieve/receive one or more hanging protocols from server 130. For example, a default hanging protocol may be communicated to display workstation 140 from server 130.

Display devices 140 may present one or more imaging studies according to a hanging protocol. As described above, a hanging protocol is a set of display rules for presenting, formatting, and otherwise organizing images on a display device of a display device 140. A display rule is a convention for presenting one or more images in particular temporal and/or spatial layout or sequence. For example, a hanging protocol may include a set of computer-readable instructions (or display rules, for example) that direct a computer to display a plurality of images in certain locations on a display device and/or display the plurality of images in a certain sequence or order. In another example, a hanging protocol may include a set of computer-readable instructions that direct a computer to place a plurality of images in multiple screens and/or viewing areas on a display device 140. In general, a hanging protocol may be employed to present a plurality of images for a diagnostic examination of a patient anatomy featured in the images.

A hanging protocol may direct, for example, a display device 140 to display an anterior-posterior ("AP") image adjacent to a lateral image of the same patient anatomy. In another example, a hanging protocol may direct display device 140 to display the AP image before displaying the lateral image (in other words, prior in time). In general, a hanging protocol dictates the spatial and/or temporal presentation of a plurality of images in one or more imaging studies at a display device 140. A hanging protocol may also be used to select images and/or imaging studies to present at display device 140.

As discussed above, the components, elements, and/or functionality of the PACS system 100 may be implemented alone or in combination in various forms in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Figure 2:
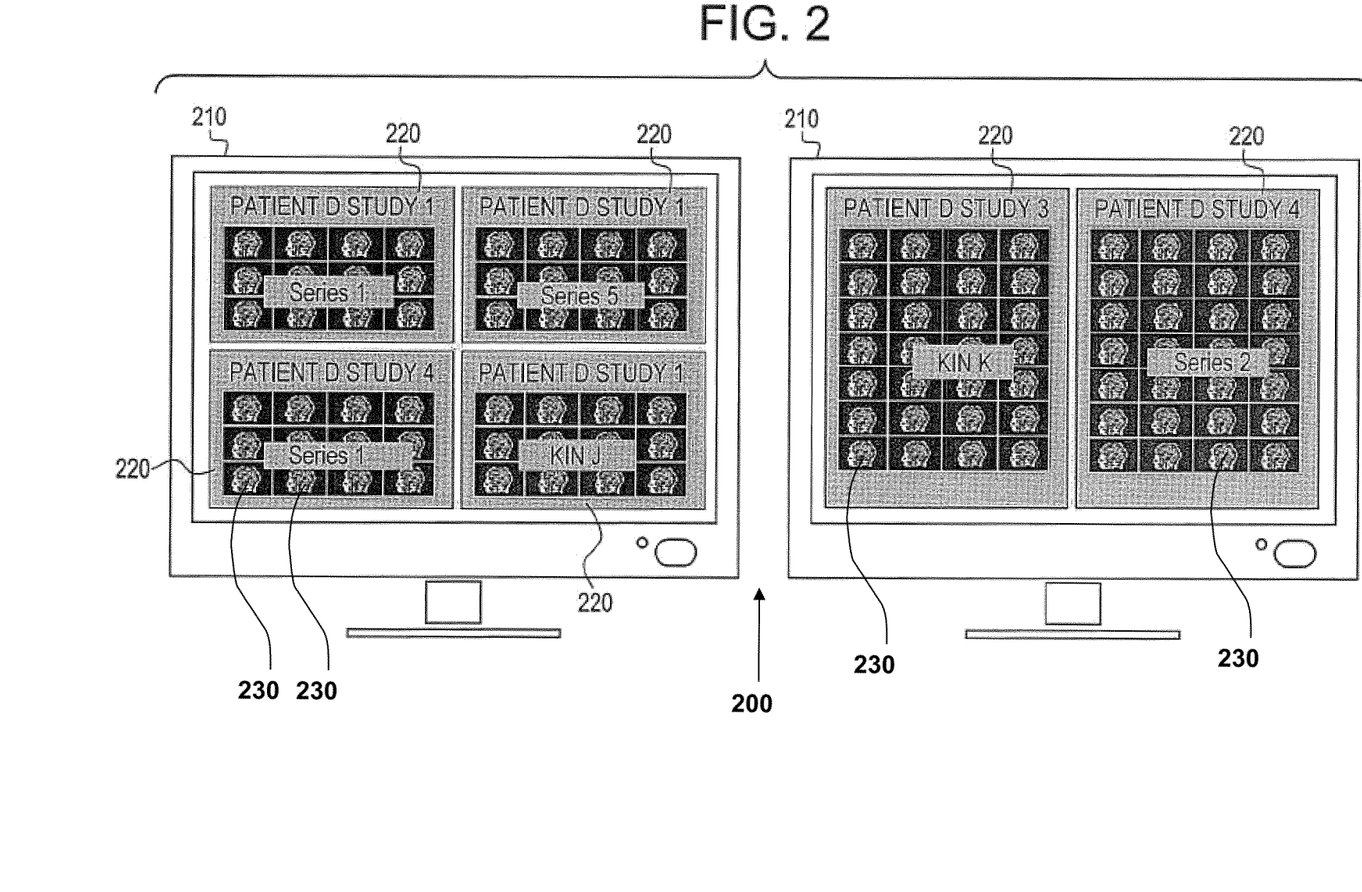
FIG. 2 illustrates an exemplary PACS display device according to an embodiment of the present invention.

FIG. 2 illustrates an exemplary PACS display device 200, such as the display device 140 of the PACS system 100, according to an embodiment of the present invention. The display device 200 includes two monitors 210 and six image regions 220, although any number of monitors 210 and image regions 220 may be implemented. The image regions 220 may include one or more images 230. For example, the images shown in FIG. 2 are for STUDY 1, STUDY 3, and STUDY 4 of PATIENT D.

In certain embodiments of the present invention, the one or more images may be matched on, loaded, and/or displayed based at least in part on the image hanging protocol. In certain embodiments, the one or more images may be automatically matched on, loaded, and/or displayed.

In certain embodiments of the present invention, the image hanging protocol matches on, loads, and/or displays a study of a patient, as described below. For example, the image region 220 in the upper left-hand corner of the left monitor displays images associated with SERIES 1 of STUDY 1. As another example, the image region 220 on the right-hand side of the right monitor displays images associated with SERIES 2 of STUDY 4.

In certain embodiments of the present invention, the image hanging protocol matches on, loads, and/or displays a key image note ("KIN"), as described below. For example, the image region 220 in the lower right-hand corner of the left monitor displays images associated with KIN J of STUDY 1. As another example, the image region 220 on the left-hand side of the right monitor displays images associated with KIN K of STUDY 3.

As discussed above, the components, elements, and/or functionality of the display device 200 may be implemented alone or in combination in various forms in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Figure 3:
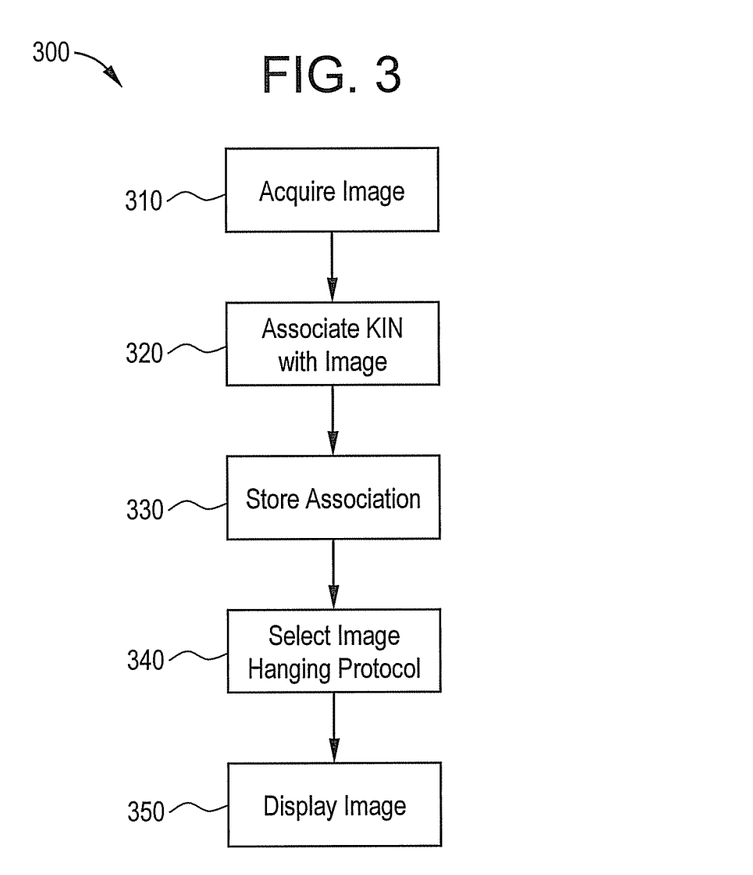
FIG. 3 illustrates an image display method according to an embodiment of the present invention.

FIG. 3 illustrates an image display method 300 according to an embodiment of the present invention. The method 300 includes the following steps, which are described below in more detail. At step 310, an image set is acquired. At step 320, a key image note is associated with the acquired image set. At step 330, the acquired image set and/or the associated key image note are stored. At step 340, an image hanging protocol is selected. At step 350, one or more images are displayed based at least in part on the selected imaging hanging protocol. The method 300 is described with reference to the elements of the PACS system 100 described above, but it should be understood that other implementations are possible.

At step 310, an image set is acquired. The image set may be acquired by the PACS system 100. More particularly, the image set may be acquired by the imaging modality 110 of the PACS system 100. The image set may include one or more images.

At step 320, a KIN is associated with the acquired image set. For example, a study may contain 200 images; a "For Teaching" KIN may reference 5 of the 200 images, where the 5 images are considered important during teaching. As another example, another KIN may reference another subset of the 200 images, some of which may be the images also referenced by the first 5-image KIN.

The KIN may be associated with the acquired image set by the PACS system 100. More particularly, the KIN may be associated with the acquired image set by the acquisition workstation 120 of the PACS system 100. Alternatively, the KIN may be associated with the acquired image set by the network server 130 of the PACS system 100. The acquired image set may be the image set acquired at step 310.

The KIN may include a title, and optionally a subtitle, a creation date, a creation time, a creator, and/or a creator type. Table 1 includes several examples of KIN categories or types.

TABLE 1

KIN Examples

| | Study | KIN Title | KIN Subtitle | Creation Date/Time | Creator/Creator Type |
|---|---|---|---|---|---|
| KIN_1 | Study A | For Surgery | | 2005.09.17 10:27 | Smith, John Radiologist |
| KIN_2 | Study A | For Conference | Brain Images | 2005.09.12 08:46 | Doe, Mary Instructor |
| KIN_3 | Study A | For Conference | Neck/Head Images | 2005.04.28 14:31 | Smith, John Radiologist |
| KIN_4 | Study A | For Patient | | 2005.03.11 12:08 | Green, Jane Radiologist |
| KIN_5 | Study B | For Surgery | | 2004.10.18 16:58 | Brown, Mark Clinician |
| KIN_6 | Study B | For Peer Review | | 2004.10.18 16:45 | Brown, Mark Clinician |

In certain embodiments of the present invention, the KIN may be created and/or selected by a user, such as a healthcare provider (e.g., surgeon, radiologist, clinician, analyst, physician) and/or a patient.

At step 330, the acquired image set and/or the associated KIN are stored. The acquired image set and the associated KIN may be stored by the PACS system 100. More particularly, the acquired image set and the associated KIN may be stored by the acquisition workstation 120 of the PACS system 100. Alternatively, the acquired image set and the associated KIN may be stored by the network server 130 of the PACS system 100. The acquired image set may be the image set acquired at step 310. The associated KIN may be the KIN associated at step 320.

Alternatively, the relationship between the acquired image set and the associated KIN may be stored at step 330. That is, the acquired image set and/or the associated KIN may be stored prior to step 330. For example, the acquired image set may be stored at step 310. As another example, the associated KIN may be stored prior to performing the steps 310-350 of the method 300.

At step 340, an image hanging protocol is selected. The image hanging protocol may include a rule set. The rule set may include one or more rules. For example, the rule set may include a rule for selecting a KIN. As another example, the rule set may include a rule for loading one or more images associated with the selected KIN. As another example, the rule set may include a rule for displaying one or more images associated with a selected KIN.

In certain embodiments of the present invention, the image hanging protocol may be created and/or selected by a user, such as a healthcare provider (e.g., surgeon, radiologist, clinician, analyst, physician) and/or a patient. For example, a surgeon may set up an image hanging protocol to view all images marked with a KIN Title of "For Surgery". As another example, a radiologist at a teaching institution may set up an image hanging protocol to display all images marked with a KIN Title of "For Teaching" and a KIN Subtitle of "Brain Malignancy". As another example, a clinician may set up an image hanging protocol to display the most recent KIN created by radiologists, viewing the KINs one at a time. As another example, an analyst of disease progression may set up an image hanging protocol to view and compare "For Research" KIN images from a current study and corresponding "For Research" KIN images from a historical study. As another example, a physician may set up an image hanging protocol to display all of the images marked with a KIN to review all of the images of significance.

In certain embodiments of the present invention, the image hanging protocol may be created and/or selected by a system, such as the PACS system 100 of FIG. 1. For example, a user issues a command to display an exam, and the system automatically selects the hanging protocol, applies it (e.g., matches on images, comparison studies, KINs, etc.), and displays the images.

In certain embodiments of the present invention, the image hanging protocol may "MATCH ON" and/or "LOAD" not only a study, but also a KIN. "MATCHING ON" a KIN refers to matching a selected KIN with one or more images associated with the selected KIN. "MATCHING ON" a KIN may also refer to applying a set of matching rules to determine which images and/or KINs are most desirable for loading and/or display. "MATCHING ON" a KIN category refers to matching a selected KIN category with one or more images associated with the selected KIN category.

"LOADING" a KIN refers to loading and/or displaying one or more images associated matched on by the image handing protocol. That is, "LOADING" a KIN refers to loading and/or displaying one or more images associated with the selected KIN. "LOADING" a KIN category refers to loading and/or displaying one or more images associated with the selected KIN category.

In certain embodiments of the present invention, one or more images may be automatically matched on, loaded, and/or displayed based at least in part on the KIN and/or the KIN category.

In certain embodiments of the present invention, matching rules for a KIN may be defined by the image hanging protocol in much the same way that matching rules for a study are defined by the image hanging protocol. However, matching rules for a KIN are based at least in part on KIN-specific characteristics, such as title, subtitle, creation date, creation time, creator, creator type, and study level (e.g. current/historical study).

In certain embodiments of the present invention, the matching rules may include different modes, such as an "AT LEAST ONE" mode and an "ALL" mode. For example, the "AT LEAST ONE" mode would yield a match if a KIN matches on at least one of a KIN-specific characteristics. As another example, the "ALL" mode would yield a match only if a KIN matches on all of the KIN-specific characteristics.

In certain embodiments of the present invention, the image hanging protocol may match on more than one KIN, resulting in a conflict. The image hanging protocol may resolve this conflict in a variety of ways. For example, the match may be determined based at least in part on the KIN creation date (e.g., most/least recent), yielding a single match. As another example, the match may be determined based at least in part on "ALL" matched KINs, yielding multiple matches.

Several examples of image hanging protocols, matching rules, and corresponding matches are provided below. The examples are based at least in part on Table 1, as provided above. Table 1 includes a list of KINs for STUDY A, a current study of a patient, and STUDY B, a corresponding historical study of the same patient.

For simplicity, when we say that a hanging protocol matches on a particular KIN, we mean that an image region in the image hanging protocol has its matching rules set to match on the KIN. Additionally, in these examples, every image hanging protocol has only one image region matching on a KIN to avoid confusion, although an image hanging protocol may include any number of image regions matching on various KINs.

Example 1

Hanging Protocol HP__1 defines the following rule(s) matched in an "ALL" fashion:
KIN Title(s): For Conference
KIN Subtitle(s): Neck/Head Images
Current Study
The match yields {KIN__3}.

Example 2

Hanging Protocol HP__2 defines the following rule(s) matched in an "ALL" fashion:
Creator Type: Radiologist
Current study
The match yields {KIN__1, KIN__3, KIN__4}, which if "most recent creation date/time" is applied, the result is KIN__1.

Example 3

Hanging Protocol HP__3 defines the following rule(s) matched in an "ALL" fashion:
KIN Title: For Surgery
First historical study
The match yields {KIN__6}.

Example 4

Hanging Protocol HP__4 defines the following rule(s) matched in an "ANY" fashion:
KIN Title: For Surgery
The match yields {KIN__1, KIN__5}, which if "least recent creation date/time" is applied, the result is KIN__5.

Example 5

Hanging Protocol HP__5 defines no matching rules:
The rule yields {KIN__1, KIN__2, KIN__3, KIN__4, KIN__5, KIN__6}, which if "most recent creation date/time" is applied, the result is KIN__1, whereas if "least recent creation date/time" is applied, the result is KIN__6.

At step 350, one or more images are displayed based at least in part on the selected image hanging protocol. The images may be displayed by the PACS system 100. More particularly, the images may be displayed by the display device 140 of the PACS system 100. The one or more images may include the image set acquired at step 310, the image set associated with a KIN at step 320, and/or the image set stored at step 330.

One or more of the steps of the method 300 may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Certain embodiments of the present invention may omit one or more of these steps and/or perform the steps in a different order than the order listed. For example, some steps may not be performed in certain embodiments of the present invention. As a further example, certain steps may be performed in a different temporal order, including simultaneously, than listed above.

Figure 4:
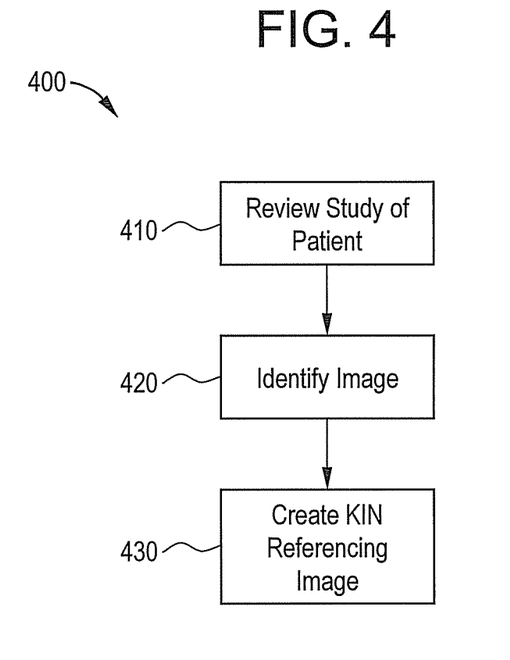
FIG. 4 illustrates a flow chart of an exemplary KIN creation workflow according to an embodiment of the present invention.

FIG. 4 illustrates a flow chart of an exemplary KIN creation workflow 400 according to an embodiment of the present invention. The workflow 400 includes the following steps, which are described below in more detail. At step 410, a radiologist reviews a study of a patient. At step 420, the radiologist identifies a set of images. At step 430, the radiologist creates a KIN referencing the image set. The workflow 400 is described with reference to the elements of the PACS system 100 and the steps of the image display method 300, but it should be understood that other implementations are possible.

At step 410, a radiologist reviews a study of a patient. That is, the radiologist navigates through the images in the study of the patient. The study of the patient may be reviewed using the PACS system 100.

At step 420, the radiologist identifies a set of images. For example, the radiologist may identify 3 images to be used during surgery. As another example, the radiologist may identify 5 images to be used in conferences and/or reviews. As another example, the radiologist may identify 1 image to be passed on to a patient. The images may be the images in the study of the patient that was reviewed at step 410.

At step 430, the radiologist creates a KIN referencing the image set. For example, the radiologist may create a "For Surgery" KIN referencing the 3 images to be used during surgery. As another example, the radiologist may create a "For Conference" KIN referencing the 5 images to be used in conferences and/or reviews. As another example, the radiologist may create a "For Patient" KIN referencing the 1 image to be passed on to the patient. The image set may be the set of images identified at step 420.

One or more of the steps of the KIN creation workflow 400 may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Certain embodiments of the present invention may omit one or more of these steps and/or perform the steps in a different order than the order listed. For example, some steps may not be performed in certain embodiments of the present invention. As a further example, certain steps may be performed in a different temporal order, including simultaneously, than listed above.

Figure 5:
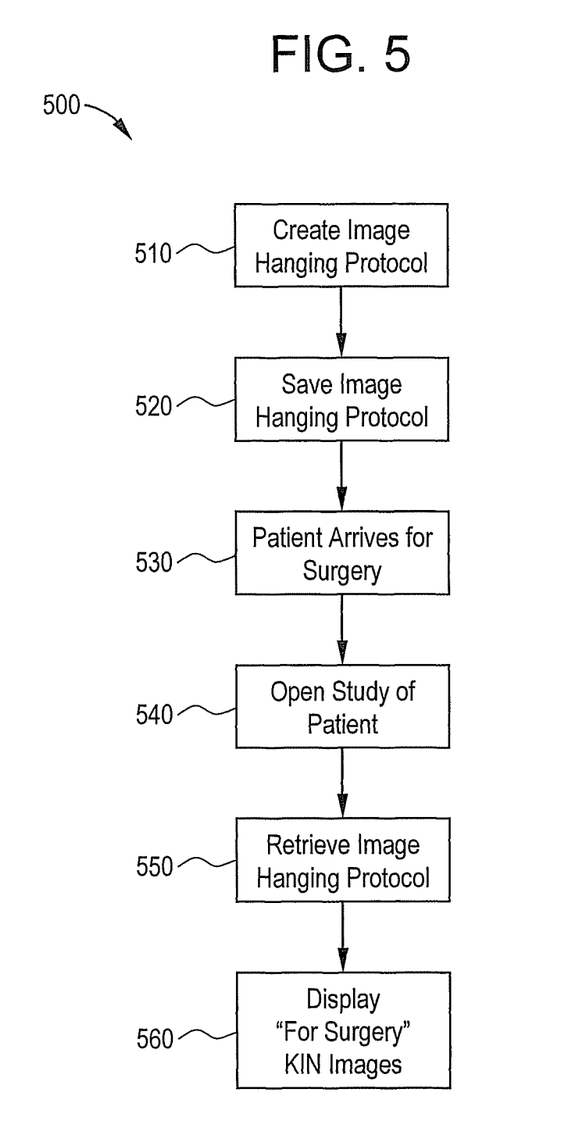
FIG. 5 illustrates an exemplary surgical review workflow according to an embodiment of the present invention.

FIG. 5 illustrates an exemplary surgical review workflow 500 according to an embodiment of the present invention. The workflow 500 includes the following steps, which are described below in more detail. At step 510, a surgeon creates an imaging hanging protocol to display "For Surgery" KIN images. At step 520, the image hanging protocol is saved. At step 530, a patient arrives for surgery. At step 540, the surgeon opens a study of the patient. At step 550, the image hanging protocol is retrieved. At step 560, the "For Surgery" KIN images are displayed. The workflow 500 is described with reference to the elements of the PACS system 100 and the steps of the image display method 300, but it should be understood that other implementations are possible.

At step 510, a surgeon creates an imaging hanging protocol to display "For Surgery" KIN images. At step 520, the image hanging protocol is saved. Alternatively, the surgeon may select a predefined image hanging protocol. The image hanging protocol may be created, selected, and/or saved using the PACS system 100. The image hanging protocol may be the image hanging protocol selected at step 340 of the method 300. The "For Surgery" KIN may be the KIN created at step 430 of the KIN creation workflow 400.

At step 530, a patient arrives for surgery. At step 540, the surgeon opens a study of the patient. At step 550, the image hanging protocol is retrieved. At step 560, the "For Surgery" KIN images are displayed. For example, the 3 images marked with the "For Surgery" KIN created at step 430 of the workflow 400 for KIN creation is displayed at step 560 of the workflow 500 for surgical review.

Steps 540-560 of the workflow 500 may be performed using the PACS system 100. In certain embodiments of the present invention, steps 540-560 of the workflow 500 may be automated. For example, the "for surgery" KIN images may be displayed automatically at step 560.

One or more of the steps of the surgical review workflow 500 may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Certain embodiments of the present invention may omit one or more of these steps and/or perform the steps in a different order than the order listed. For example, some steps may not be performed in certain embodiments of the present invention. As a further example, certain steps may be performed in a different temporal order, including simultaneously, than listed above.

Figure 6:
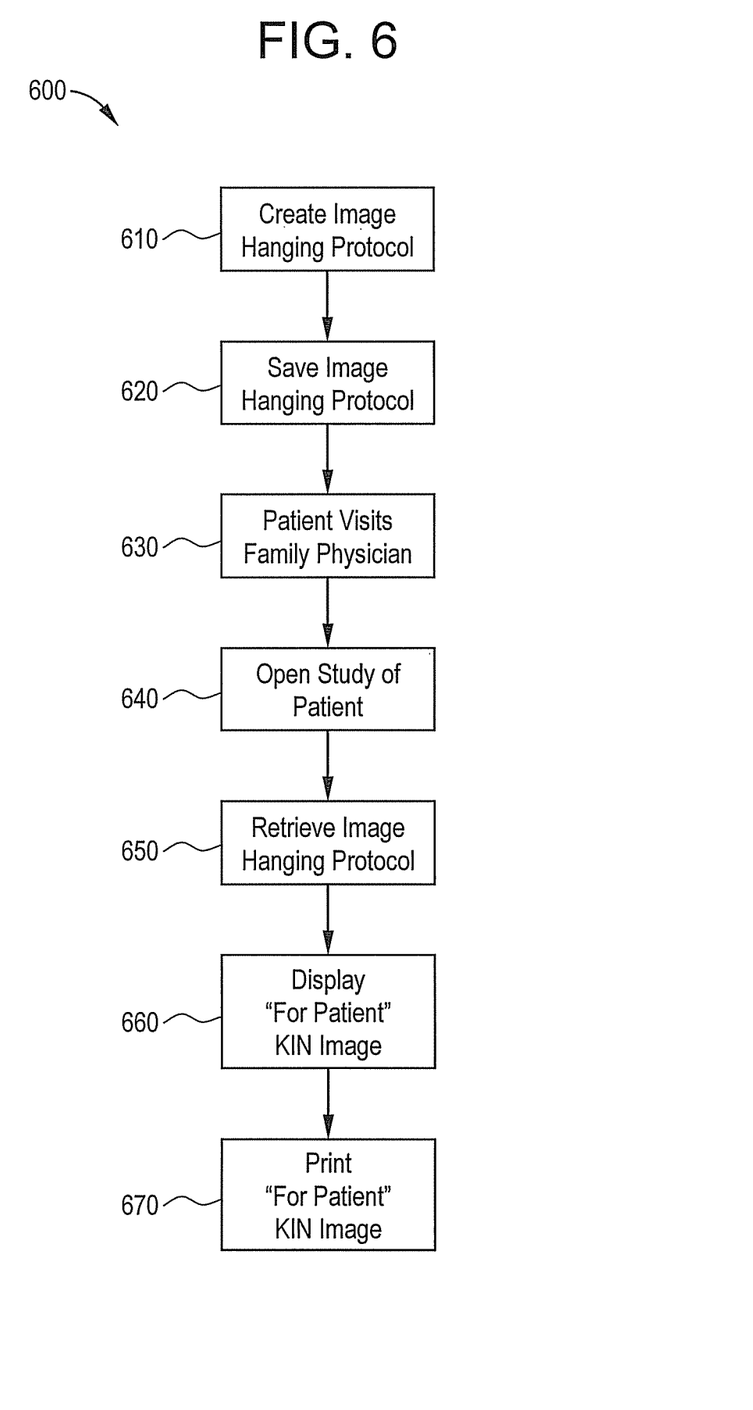
FIG. 6 illustrates an exemplary patient consultation and referral workflow according to an embodiment of the present invention.

FIG. 6 illustrates a flow chart of an exemplary patient consultation and referral workflow 600 according to an embodiment of the present invention. The workflow 600 includes the following steps, which are described below in more detail. At step 610, a family physician creates an image hanging protocol to display "For Patient" KIN images. At step 620, the image hanging protocol is saved. At step 630, a patient visits the family physician. At step 640, the family physician opens a study of the patient. At step 650, the image hanging protocol is retrieved. At step 660, the "For Patient" KIN images are displayed. At step 670, the physician prints the "For Patient" KIN images for the patient. The workflow 600 is described with reference to the elements of the PACS system 100 and the steps of the image display method 300, but it should be understood that other implementations are possible.

At step 610, a family physician creates an image hanging protocol to display "FOR PATIENT" KIN images. At step 620, the image hanging protocol is saved. Alternatively, the family physician may select a predefined image hanging protocol. The image hanging protocol may be created, selected, and/or saved using the PACS system 100. The image hanging protocol may be the image hanging protocol selected at step 340 of the method 300. The image hanging protocol may be the image hanging protocol selected at step 340 of the method 300. The "For Patient" KIN may be the KIN created at step 430 of the KIN creation workflow 400.

At step 630, a patient visits the family physician. At step 640, the family physician opens a study of the patient. At step 650, the image hanging protocol is retrieved. At step 660, the "For Patient" KIN images are displayed. At step 670, the physician prints the "For Patient" KIN images for the patient. For example, the 1 image marked with the "For Patient" KIN created at step 430 of the workflow 400 for KIN creation is displayed at step 660 of the workflow 600 for patient consultation and referral.

Steps 610-670 of the workflow 600 may be performed using the PACS system 100. In certain embodiments of the present invention, steps 640-670 of the workflow 600 may be automated. For example, the "for patient" KIN images may be displayed automatically at step 660.

One or more of the steps of the patient consultation and referral workflow 600 may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Certain embodiments of the present invention may omit one or more of these steps and/or perform the steps in a different order than the order listed. For example, some steps may not be performed in certain embodiments of the present invention. As a further example, certain steps may be performed in a different temporal order, including simultaneously, than listed above.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A computer-implemented image display method including:
    accepting a user selection of an image hanging protocol configured to display a subset of a plurality of medical diagnostic images associated with a patient anatomy for review by the user in support of patient diagnosis, wherein one or more of the plurality of images is associated with a key image note marking the image and specifying a clinical significance of the image with respect to patient diagnosis, and wherein the image hanging protocol includes a rule set for displaying the subset of images to the user for patient diagnosis based at least in part on the key image note;
    determining, based on the user selection of the image hanging protocol, the subset of images specified by the rule set of the image hanging protocol based at least in part on the key image note;
    automatically loading, using a processor, the subset of images with key image notes matching the key image note specified by the image hanging protocol; and
    displaying, using the processor, the subset of images based at least in part on the image hanging protocol.

2. The method of claim 1, wherein the key image note includes at least one of a title, a subtitle, a creation date, a creation time, a creator, a creator type, and a study level.

3. The method of claim 1, wherein the rule set includes a rule for loading the key image note.

4. The method of claim 1, wherein the rule set includes a rule for automatically displaying the image set based at least in part on the key image note.

5. The method of claim 4, wherein the displaying step includes automatically displaying the subset of images based at least in part on the image hanging protocol.

6. The method of claim 1, further including acquiring the image set.

7. The method of claim 1, further including associating the subset of images with the key image note.

8. The method of claim 1, further including storing the subset of images and the key image note.

9. The method of claim 1, further including storing an association between the subset of images and the key image note.

10. An image display system including:
    a display device adapted to display an image set of medical diagnostic images of a patient anatomy based at least in part on an image hanging protocol, the images to be reviewed by a user in support of patient diagnosis, the display device including a processor to process the image hanging protocol and display the image set, the image hanging protocol configured to display an image set from a patient exam that is a subset of all the images in the exam, wherein one or more of the images in the exam is associated with a key image note marking the image and specifying a clinical significance of the image with respect to patient diagnosis, and wherein the image hanging protocol includes a rule set for displaying the image set to the user for patient diagnosis based at least in part on a key image note, the rule set used by the image hanging protocol and the display device to, based on user selection of the image hanging protocol, automatically identify and load the image set having key image notes that match the key image note specified by the rule set of the image hanging protocol.

11. The system of claim 10, wherein the key image note includes at least one of a title, a subtitle, a creation date, a creation time, a creator, a creator type, and a study level.

12. The system of claim 10, wherein the image hanging protocol includes a rule for loading the key image note.

13. The system of claim 10, wherein the rule set includes a rule for automatically displaying the image set based at least in part on the key image note.

14. The system of claim 12, wherein the display device is adapted to automatically display the image set based at least in part on the image hanging protocol.

15. The system of claim 10, further including an imaging modality adapted to acquire the image set.

16. The system of claim 10, further including an acquisition workstation adapted to associate the image set with the key image note.

17. The system of claim 10, further including a network server adapted to store the image set and the key image note.

18. The system of claim 10, further including a network server adapted to store an association between the image set and the key image note.

19. The system of claim 10, wherein the system is a picture archiving and communication system.

20. A non-transitory computer-readable storage medium including a set of instructions for execution on a computer, the set of instructions including:
    an image display routine configured to display a subset of medical diagnostic images of a patient anatomy based at least in part on an image hanging protocol, the images to be reviewed by a user in support of patient diagnosis,
        wherein each of the subset of images is associated with a key image note marking the image and specifying a clinical significance of the image with respect to patient diagnosis, and
        wherein the image hanging protocol is configured to display the subset of images,
    wherein the image hanging protocol includes a rule set for displaying the subset of images to the user for patient diagnosis based at least in part on a key image note, the rule set used by the image hanging protocol to, based on user selection of the image hanging protocol, automatically identify and load the subset of images having key image notes that match the key image note specified by the rule set of the image hanging protocol.

21. A system comprising:

a processor associated with a memory storing instructions for execution using the processor, the memory including:

an image hanging protocol including a rule set for displaying an image set of medical diagnostic images using a display device based at least in part on a key image note, the images to be reviewed by a user in support of patient diagnosis, the image hanging protocol automatically selected based on a command to display an exam comprising a plurality of images of a patient anatomy to the user for patient diagnosis, the image hanging protocol configured to display an image set from the exam that is a subset of all the images in the exam, wherein the key image note indicates a clinical significance of the image with respect to patient diagnosis and includes at least one of a title, a subtitle, a creation date, a creation time, a creator, a creator type, and a study level, and wherein the rule set includes a rule for matching on the key image note such that the rule set used by the image hanging protocol to, based on user selection of the image hanging protocol, automatically identify and load the image set from the exam having key image notes that match the key image note specified by the rule set of the image hanging protocol.

22. The system of claim 21, wherein the rule set includes a rule for loading a key image note.

23. The system of claim 21, wherein the rule set includes a rule for automatically displaying the image set based at least in part on the key image note.

* * * * *